United States Patent [19]

Irikura

[11] 4,026,902
[45] May 31, 1977

[54] ISOXAZOLE DERIVATIVES
[75] Inventor: Tsutomu Irikura, Tokyo, Japan
[73] Assignee: Kyorin Pharmaceutical Co., Ltd., Tokyo, Japan
[22] Filed: June 4, 1976
[21] Appl. No.: 692,908
[30] Foreign Application Priority Data
  June 21, 1975 Japan .................. 50-76176
[52] U.S. Cl. .................. 260/307 H; 424/272
[51] Int. Cl.² .................. C07D 261/10
[58] Field of Search .................. 260/307 H
[56] References Cited
UNITED STATES PATENTS
3,752,819  8/1973  Philippe .................. 260/295 R

*Primary Examiner*—Raymond V. Rush
*Attorney, Agent, or Firm*—Armstrong, Nikaido & Marmelstein

[57] ABSTRACT

Isoxazole derivatives of the formula

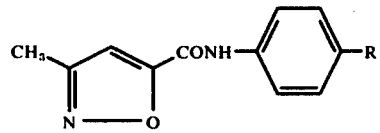

wherein R is carboxy, ethoxycarbonyl or carbamoyl, are disclosed. The compounds have utility as antidiabetic agents.

4 Claims, No Drawings

ISOXAZOLE DERIVATIVES

DETAILED DESCRIPTION

The present invention relates to compounds of the general formula: [II]:

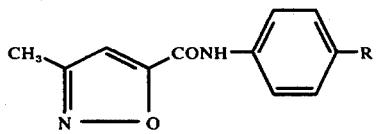

in which R represents carboxy, ethoxycarbonyl or carbamoyl, and to processes for producing the compounds [II]. The compounds of the present invention are useful as antidiabetic agents and can be prepared as follows: A compound of the general formula [I]:

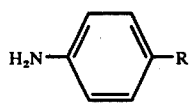

in which R is the same as above, may be reacted with 3-methylisoxazole-5-carbonyl chloride in the presence of appropriate acid acceptor such as, for example, potassium carbonate, triethylamine, and so on, in an appropriate solvent such as, for example, acetone, chloroform, and so on, at room temperature or at the boiling point of the solvent, and very smoothly to provide an isoxazole derivative having the general formula [II]:

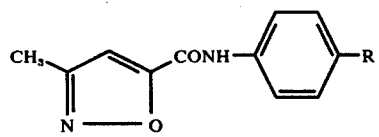

in which R is the same as above.

The present compounds reduce the blood sugar levels in intact and alloxan diabetic rats with slight administration. Further, the present compounds have FFA reducing action. But it was difficult to find the rebound of reducing serum free fatty acid levels as seen for pyrazole derivatives. On the example compounds, these results are described as follows.

LOWERING OF BLOOD SUGARS IN INTACT RATS

Male rats of the Sprague Dowley strain were used in this experiment. The hypoglycemic potency was determined in intact rats weighing 180 to 200g, following a 18-hour fast. The rats were injected subcutaneously with 100 mg glucose/150g b.w. immediately after 25 mg/kg of the present compound was administered orally. Blood was withdrawn from the tail vein at 2 and 5 hours after treatments. Blood sugars were determined by Momose's method. Results are shown in Table 1. The present compounds were more effective than tolbutamide.

LOWERING OF BLOOD SUGARS IN ALLOXAN DIABETIC RATS

The hypoglycemic effect of the present compounds was determined in 220g Sprague Dowley alloxan diabetic rats that had been injected intravenously with 50 mg/kg of alloxan monohydrate 48 hours prior to use, and had blood sugars ranging from 270 mg% to 500 mg%. Blood was withdrawn from the tail vein 2, 4 and 6 hours after the present compounds were administered orally 25 mg/kg in feed. Blood sugars were determined by Momose's method.

As shown in Table 2, the blood sugars of alloxan diabetic rats treated with the present compounds were continuously depressed 6 hours after low-dose (25 mg/kg) treatment.

RECOVERY FROM REDUCED SERUM FREE FATTY ACIDS

Male Sprague Dawley rats weighing about 190g were used. Rats were pretreated orally with 25 mg/kg of the present compounds for 4 days. After the last dose on day 4, the rats were fasted over night. On the morning of the fifth day, the rats were administered orally 12.5 mg/kg of the present compound. Immediately following oral treatment on day 5, all rats were primed with a subcutaneous injection of 100 mg glucose/150g b.w. Serum free fatty acids were determined in duplicate by the method of Itaya-Ui at 4 hours after treatment. The results in Table 3 tend to show that it is difficult to find the rebound of the reduction of serum free fatty acid levels.

Based on these results, the present compounds are seen to be suitable for the improvements of the abnormal metabolism of blood sugars and lipids in the diabetic state.

Table 1

| | | | Blood Sugars (mg%) | | | |
| | Dose | | 2 hour | | 5 hour | |
| Compounds | (p.o.) mg/kg | No. of Animals | Mean ± S.E. | relative % | Mean ± S.E. | relative % |
|---|---|---|---|---|---|---|
| Control | — | 8 | 81.5 ± 2.0 | 100 | 81.7 ± 2.9 | 100 |
| Example 1 | 25 | 8 | 53.6**** ± 3.5 | 65.8 | 63.8**** ± 3.0 | 78.1 |
| Tolbutamide | 25 | 8 | 56.4** ± 5.9 | 69.2 | 68.2* ± 4.7 | 83.5 |
| Control | | 8 | 83.4 ± 1.8 | 100 | 84.9 ± 3.1 | 100 |
| Example 2 | 25 | 8 | 55.0**** ± 5.2 | 66.0 | 60.6**** ± 2.6 | 71.4 |
| Example 3 | 25 | 7 | 61.4**** ± 3.8 | 73.6 | 70.3*** ± 3.2 | 82.7 |
| Tolbutamide | 25 | 7 | 73.3* ± 4.2 | 87.9 | 68.0** ± 4.9 | 80.1 |

Significantly different from Control
*$P<0.05$,
**$P<0.02$,
***$P<0.01$
****$P<0.001$

Table 2

Effects of the compounds of Example 1 and 2 on the blood sugar level in Alloxan diabetic rats

| Compounds Dose(p.o.)mg/kg No. of Animals | | Control — 6 | Example 1 25 9 | Example 2 25 7 |
|---|---|---|---|---|
| Blood Sugar (mg %) | Initial | 387.4 ± 24.9 | 414.2 ± 20.4 | 408.1 ± 28.0 |
| | relative % | 100.0 | 106.9 | 105.3 |
| | 2 hour | 330.5 ± 25.3 | 308.9 ± 28.9 | 300.8 ± 31.5 |
| | relative % | 100.0 | 93.5 | 91.0 |
| | 4 hour | 330.0 ± 26.4 | 221.2 ± 31.2 | 237.3 ± 41.9 |
| | relative % | 100.0 | 73.7 | 79.1 |
| | 6 hour | 258.2 ± 32.2 | 12.5*** ± 22.7 | 156.5 ± 37.8 |
| | relative % | 100.0 | 47.4 | 60.6 |

Table 3

Recovery from reduced serum free fatty acids

| Compounds | Dose mg/kg (b.i.d.) p.o. | No. of Animals | Serum Free Fatty Acid βEg/100 ml | |
|---|---|---|---|---|
| | | | 4 hour | relative % |
| Control | — | 9 | 67.8 ± 5.3 | 100 |
| Example 1 | 25 | 9 | 63.3 ± 3.7 | 93.4 |

The invention is further illustrated by the following examples.

EXAMPLE 1

Synthesis of N-(p-carboxyphenyl)-3-methylisoxazole-5-carboxamide

To a stirred suspension of 6.9g of p-aminobenzoic acid and 3.5g of potassium carbonate in 60 ml of acetone was added 7.3g of 3-methylisoxazole-5-carbonyl chloride. The mixture was stirred at room temperature for 1 hr. and then refluxed for 1 hr. The precipitate was filtered off and dissolved in water. The solution was acidified with concentrated hydrochloride acid. The precipitate was filtered off and washed with ethanol. There was obtained 9.1g of N-(p-carboxyphenyl)-3-methylisoxazole-5-carboxamide. Melting point: above 300° C. Yield: 73.4%.

Analysis for $C_{12}H_{10}N_2O_4$:

| | C | H | N |
|---|---|---|---|
| Calcd. | 58.53 | 4.09 | 11.38 |
| Found | 58.36 | 3.88 | 11.18 |

EXAMPLE 2

Synthesis of N-(p-ethoxycarbonylphenyl)-3-methylisoxazole-5-carboxamide

To a stirred solution of 3.3g of ethyl p-aminobenzoate in 60 ml of acetone was added 1.46g of 3-methylisoxazole-5-carbonyl chloride. The mixture was stirred at room temperature for 1 hr. and then refluxed for 1 hr. The solvent was removed and the residue was washed with 5% hydrochloric acid, 5% potassium carbonate and water. Recrystallization from a mixture of benzene and n-hexane gave 1.6g of pure product. Melting point: 160°–163° C. Yield: 58.4%.

Analysis for $C_{14}H_{14}N_2O_4$:

| | C | H | N |
|---|---|---|---|
| Calcd. | 61.31 | 5.15 | 10.21 |
| Found | 61.27 | 5.10 | 10.21 |

EXAMPLE 3

Synthesis of N-(p-carbamoylphenyl)-3-methylisoxazole-5-carboxamide p-Aminobenzamide.¼¼ H₂O was worked up with 3-methyl-isoxazole-5-carbonyl chloride by the same procedure as given in Example 2 to yield N-(p-carbamoylphenyl)-3-methylisoxazole-5-carboxamide. Melting point: above 300° C. Yield: 79.1%.

Analysis for $C_{12}H_{11}N_3O_3$:

| | C | H | N |
|---|---|---|---|
| Calcd. | 58.77 | 4.52 | 17.14 |
| Found | 58.68 | 4.42 | 16.82 |

What is claimed is:
1. A compound of the formula

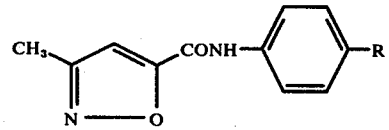

in which R is carboxy, ethoxycarbonyl or carbamoyl.
2. The compound of claim 1, N-(p-Carboxyphenyl)-3-methylisoxazole-5-carboxamide.
3. The compound of claim 1, N-(p-Ethoxycarbonylphenyl)-3-methylisoxazole-5-carboxamide.
4. The compound of claim 1, N-(p-Carbamoylphenyl)-3-methylisoxazole-5-carboxamide.

* * * * *